US008552755B2

(12) United States Patent
Wang et al.

(10) Patent No.: US 8,552,755 B2
(45) Date of Patent: Oct. 8, 2013

(54) HIGH THROUGHPUT CURRENT-VOLTAGE COMBINATORIAL CHARACTERIZATION TOOL AND METHOD FOR COMBINATORIAL SOLAR TEST SUBSTRATES

(71) Applicant: Intermolecular, Inc., San Jose, CA (US)

(72) Inventors: Yun Wang, San Jose, CA (US); Tony P. Chiang, Campbell, CA (US); Chi-I Lang, Cupertino, CA (US)

(73) Assignee: Intermolecular, Inc., San Jose, CA (US)

( * ) Notice: Subject to any disclaimer, the term of this patent is extended or adjusted under 35 U.S.C. 154(b) by 0 days.

(21) Appl. No.: 13/849,749

(22) Filed: Mar. 25, 2013

(65) Prior Publication Data

US 2013/0214808 A1    Aug. 22, 2013

Related U.S. Application Data

(63) Continuation of application No. 12/952,983, filed on Nov. 23, 2010, now Pat. No. 8,432,177.

(60) Provisional application No. 61/334,165, filed on May 12, 2010.

(51) Int. Cl.
*G01R 31/26* (2006.01)

(52) U.S. Cl.
USPC .................................... 324/761.01

(58) Field of Classification Search
USPC .......................... 324/760.01–760.02, 761.01, 324/762.01–762.1; 257/48; 438/14–18; 703/18
See application file for complete search history.

(56) References Cited

U.S. PATENT DOCUMENTS 7,309,850 B2 * 12/2007 Sinton et al. ................ 250/203.4
8,315,845 B2 * 11/2012 Lepage ............................ 703/6

* cited by examiner

*Primary Examiner* — Tung X Nguyen

(57) ABSTRACT

Measuring current-voltage (I-V) characteristics of a solar cell using a lamp that emits light, a substrate that includes a plurality of solar cells, a positive electrode attached to the solar cells, and a negative electrode peripherally deposited around each of the solar cells and connected to a common ground, an articulation platform coupled to the substrate, a multi-probe switching matrix or a Z-stage device, a programmable switch box coupled to the multi-probe switching matrix or Z-stage device and selectively articulating the probes by raising the probes until in contact with at least one of the positive electrode and the negative electrode and lowering the probes until contact is lost with at least one of the positive electrode and the negative electrode, a source meter coupled to the programmable switch box and measuring the I-V characteristics of the substrate.

20 Claims, 10 Drawing Sheets

HIGH THROUGHPUT CURRENT-VOLTAGE COMBINATORIAL CHARACTERIZATION TOOL AND METHOD FOR COMBINATORIAL SOLAR TEST SUBSTRATES

CROSS-REFERENCE TO RELATED APPLICATION

This application claims priority to U.S. patent application Ser. No. 12/952,983, filed Nov. 23, 2010, entitled "High Throughput Current-Voltage Combinatorial Characterization Tool and Method for Combinatorial Solar Test Substrates," now U.S. Pat. No. 8,432,177 which claims priority to U.S. Provisional Patent Application No. 61/334,165, filed May 12, 2010, entitled "High Throughput Combinatorial Characterization Tool for Combinatorial Solar Test Substrates," both of which are incorporated by reference herein in their entirety.

BACKGROUND

1. Technical Field

The embodiments herein generally relate to solar processing and characterization, and more specifically, to a high throughput combinatorial characterization tool for combinatorial solar test substrates.

2. Description of the Related Art

Some exemplary solar processing operations include operations for adding (depositions) and removing layers (etch), defining features, preparing layers (e.g., cleans), doping, etc. However, solar companies conduct research and development (R&D) on full substrate processing, often on very large substrates and requiring a complete solar cell manufacturing line. This approach has resulted in high R&D costs and the inability to conduct extensive experimentation in a timely and cost effective manner. Combinatorial processing as applied to solar manufacturing operations enables multiple experiments to be performed on a single substrate and without a complete solar cell manufacturing line. Equipment for performing the combinatorial processing and characterization of the combinatorial test substrates must support the efficiency offered through the combinatorial processing operations.

Combinatorial processing enables rapid evaluation of solar processing operations. The systems supporting the combinatorial processing are flexible to accommodate the demands for running the different processes either in parallel, serial, or some combination of the two. A valuable component of the systems for combinatorial processing are the characterization tools used to produce the data from high throughput experimentation in such a way that the process does not slow down. High performance combinatorial characterization tools are needed to quickly process and characterize the combinatorial test substrates.

Conventional solar electrical characterizations, such as current vs. voltage measurements in an R&D environment, are performed independently of one another in a manual and sequential mode. However, the conventional process tends to be time consuming and resource demanding resulting in a significant loss in testing throughput. For example, when there is a need for measuring multiple sites per sample, the throughput and resources of the operators becomes a critical issue. Taking 32 sites per sample as an example, it takes several minutes to measure the current vs. voltage performance per site. To finish the characterization of each example, the operator has to move the sites every few minutes until every site on the sample has been tested. It is a lengthy and tiring test.

BRIEF DESCRIPTION OF THE DRAWINGS

The embodiments herein will be better understood from the following detailed description with reference to the drawings, in which.

DETAILED DESCRIPTION OF THE DRAWINGS

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

With increasing energy demands, alternative (e.g., green) energy gains more and more attention. As an important part of the research and development of solar cells, the electrical characterization of those solar cells also needs to improve. Measurement of the current-voltage (I-V) efficiency of a solar cell is a valuable parameter to judge the cell performance. It determines how efficiently the solar energy can be converted into electricity. For example, efficiency may be characterized by measuring the current-voltage curve of the cell under standard one sun illumination. According to several embodiments herein, a solar simulator is used as the light source with less than 1% spectrum difference as actual sunshine. The current generated by an illuminated solar cell is measured as the voltage scan by connecting the electrodes of the cell to a source meter.

The embodiments herein provide a high performance combinatorial characterization tool that saves both operator resources as well as test time, and offers a key function for high throughput and combinatorial research. Referring now to the drawings, and more particularly to FIGS. 1 through 9, where similar reference characters denote corresponding features consistently throughout the figures, there are shown several embodiments.

Combinatorial processing systems are only as good as the characterization available. Therefore, the high performance characterization tool described herein provides the means by which true high throughput experimentation may be accomplished. The operator burden can be minimized by test automation. The test time can be significantly reduced by parallel testing by measuring multiple sites at the same time instead of measuring one at a time. Although the high performance characterization tool described herein exhibits extraordinary utility in the field of combinatorial processing (e.g., by enabling high throughput experimentation), the embodiments herein, however, are not limited to combinatorial processing. Thus, the use of the high performance characterization tool described herein in combinatorial processing systems represents one of many valuable applications of the embodiments herein. For example, traditional solar cell experimentation and exploration methods, semiconductor manufacturing and fabrication, light emitting diode (LED) applications, flat panel display applications, characterization of photochromic materials, characterization of electrochromic materials, and characterization of thermochromic materials, among other applications, would all benefit from the high throughput and rapid characterization offered by the high performance characterization tool described herein.

Figure 1:
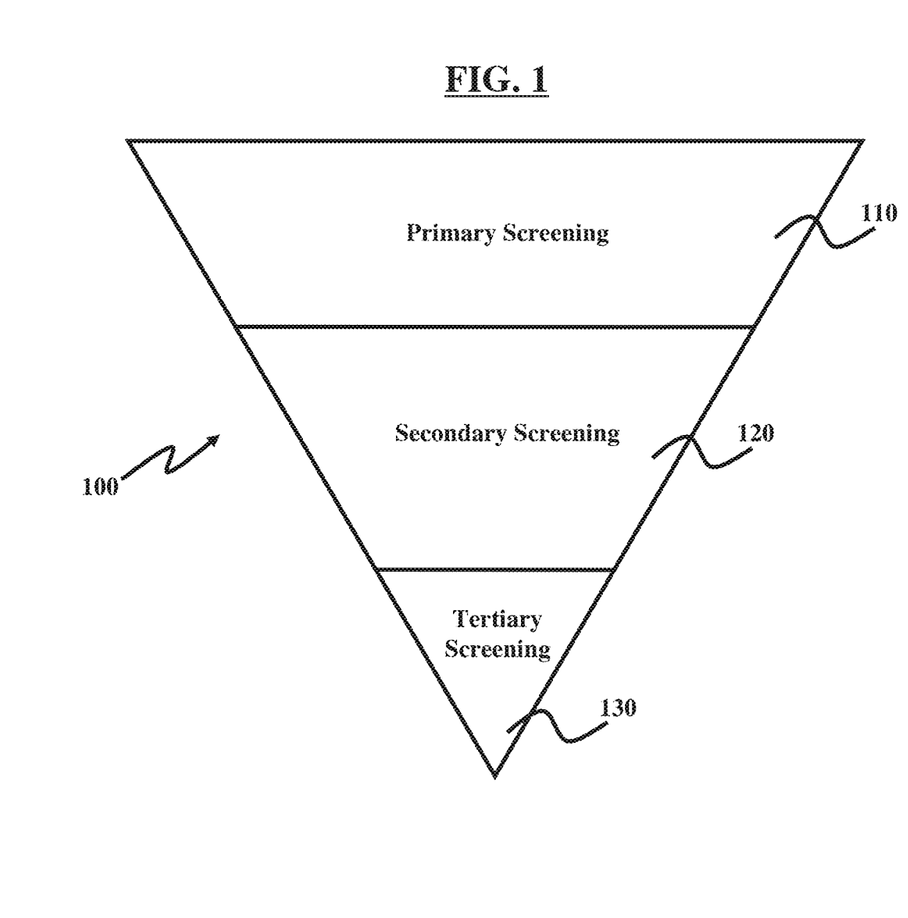
FIG. 1 illustrates a schematic diagram of a combinatorial screening process according to an embodiment herein.

As described above, during one embodiment of combinatorial processing, each wafer is subjected to many different process conditions. FIG. 1 illustrates an example of such a combinatorial screening process. As shown in FIG. 1, combinatorial screening process 100 includes primary screening process (110), secondary screening process (120), and tertiary screening process (130). In FIG. 1, for example, numerous materials compositions (e.g., 18 spots or 46 spots on a single wafer, where each spot is a unique material composition) are systematically explored on a single wafer during an initial primary screening process (110) at speeds that would otherwise be impossible using traditional methods and tools. In other words, in the embodiment shown in FIG. 1, primary screening process (110) is an initial screening that processes many samples to rule out materials for further screening. Once the best materials, process conditions, or process integration are identified using initial combinatorial screening methods (e.g., during primary screening process (110)), that material is then scaled up to test the performance (e.g., current-voltage performance) of that material and/or conditions during a secondary screening stage (e.g., secondary screening process (120)). Furthermore, according to one embodiment herein, additional testing may take place during the tertiary screening process (130). During the tertiary screening process (130), for example, the materials and/or process conditions that were not filtered out during the primary screening process (110) and the secondary screening process (120) are scaled up to a full-scale device size. Furthermore, due to the speed and non-destructiveness of the performance test (described in further detail below) occurring in the secondary screening process (120), material and/or conditions that pass both the primary screening process (110) and the secondary screening process (120) can rapidly proceed to the tertiary screening process (130). Consequently, to test the performance of these material compositions, embodiments herein utilize an improved measurement tool to enable the collection of information more rapidly.

Figure 2:
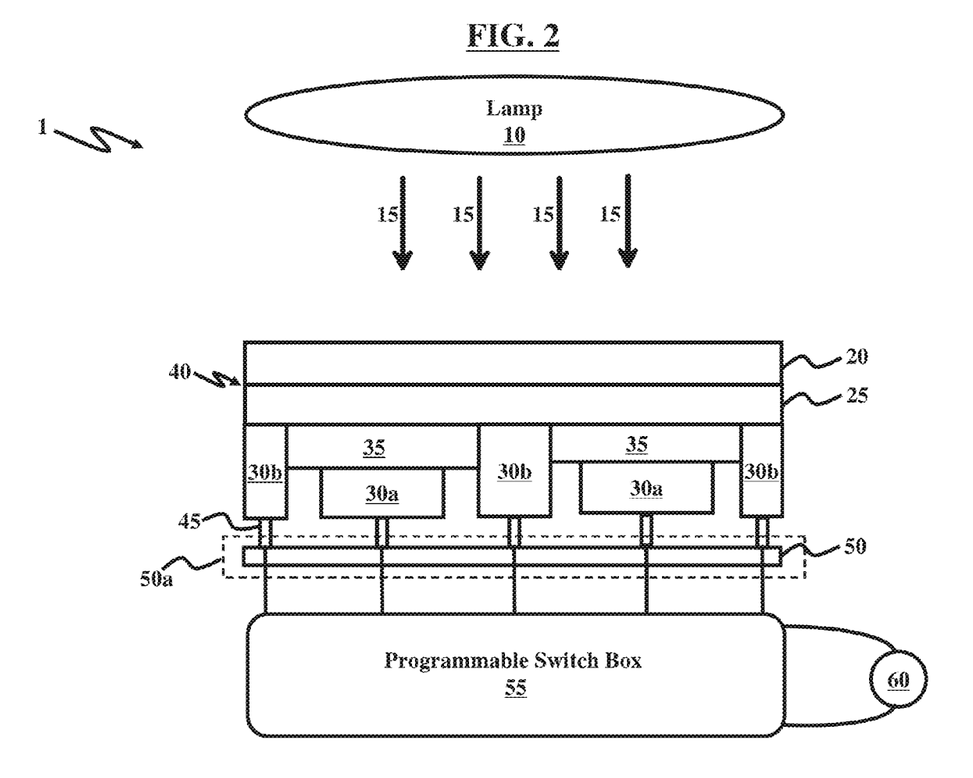
FIG. 2 illustrates a block diagram of a multi-pin combinatorial characterization apparatus according to an embodiment herein.

FIG. 2, with reference to FIGS. 1, 3B, 6A, 6B, 7, and 9, illustrates a block diagram of a multi-pin combinatorial characterization apparatus 1 according to an embodiment herein. As shown in FIG. 2, multi-pin combinatorial characterization apparatus 1 includes a lamp 10, light 15 (emitted from lamp 10), substrate 40, probes 45, switching matrix 50, programmable switch box 55, and source meter 60. The lamp 10 may comprise a solar simulator and the light 15 may comprise natural light with less than 1% difference of sunlight. As described in further detail below, substrate 40, according to one embodiment, includes glass 20, a transparent conducting oxide (TCO) coating 25, electrodes 30a, 30b, and a solar cell 35. Also shown in the embodiment of FIG. 2, the electrodes (e.g., electrodes 30a, 30b) are transferred to a back surface (e.g., TCO 25) of substrate 40 where substrate 40 is not exposed to light (e.g., light 15 emitted from lamp 10) in a configuration suitable for backside probing. While not shown in FIG. 2, those of ordinary skill in the art could reverse the configuration shown in FIG. 2 to enable frontside probing as well. In the embodiment shown in FIG. 2, each solar cell 35 of substrate 40 can be processed under varied wet (e.g. texturing) or dry (electrode sputtering, absorber layer deposition) conditions during the combinatorial processing (e.g., primary screening process (110), shown in FIG. 1). In the embodiment shown in FIG. 2 and further illustrated in FIGS. 3A and 3B, the area inside of solar cell 35 includes a positive electrode 30a while the area outside of the solar cell 35 is connected to a common electrical ground (e.g., electrode 30b). According to one embodiment herein, electrodes 30a, 30b are formed by chemical vapor deposition (CVD) and isolated by a light scribing process on substrate 40. As discussed in further detail below, light 15 generated from lamp 10 is used individually to test the performance of solar cells 35, and in one particular embodiment, the solar cells 35 may be individual site-isolated devices on a combinatorial solar test substrate 40 where each of the site-isolated devices has been varied as compared to one another. In alternate embodiments, the substrate 40 being tested may be a substrate 40 having multiple unvaried solar cells 35 produced for either commercial or research and development purposes. Examples of a solar test substrate 40 include, but are not limited to: copper indium gallium diselenide (CIGS), copper zinc tin sulfide (CZTS), and other thin film photovoltaic (TFPV) materials with a silicon or glass substrate.

Figure 9:
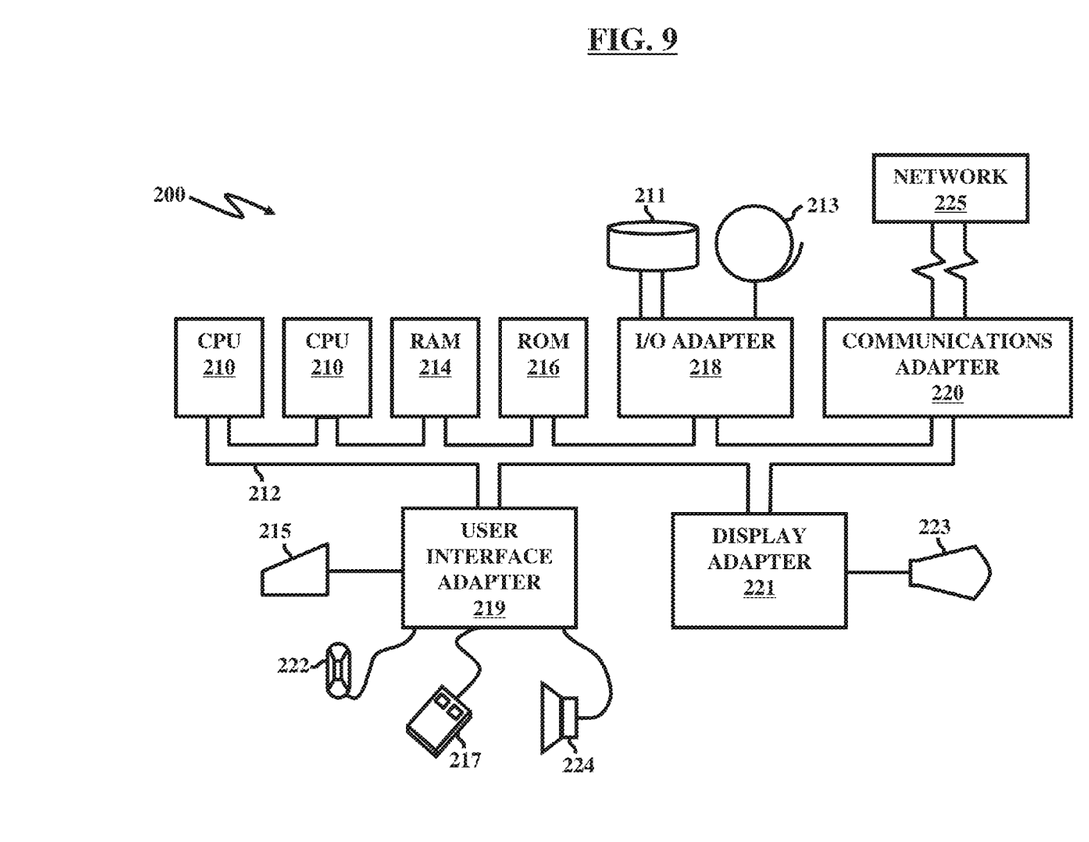
FIG. 9 illustrates a computing system according to an embodiment herein.

In addition, as shown in FIG. 2, electrodes 30a, 30b are connected to a selective circuit (e.g., switching matrix 50). In one embodiment herein, a connection between electrodes 30a and 30b is made through switching matrix 50, which is designed to match the geometry of substrate 40 with at least one probe 45 touching the inside of each solar cell 35 (e.g., electrode 30a) and the other probe 45 touching the nearby outside of each solar cell 35 (e.g., electrode 30b). For example, switching matrix 50 may include a plurality of probes 45, where each probe 45 includes a spring-loaded pin (e.g., pins 163, shown in FIG. 7) used for better contact and reduced series resistance. In addition, substrate 40 may be seated on a substrate support structure 50a and held in place by vacuum or by mechanical means, such as a clamp, or a combination of both (e.g., as further described with respect to FIGS. 6A and 6B). With a measurement device (e.g., source meter 60) operatively connected to a selective circuit (e.g., as defined by the contacts made by electrode 30a and 30b on substrate 40), a control program (e.g., as stored and executed by a computing system 200, as shown in FIG. 9) automatically selects one site (e.g., solar cell 35) on substrate 40 for testing and may continue in series with the next site (e.g., solar cell 35) until all of the sites on substrate 40 are tested.

Figure 3A:
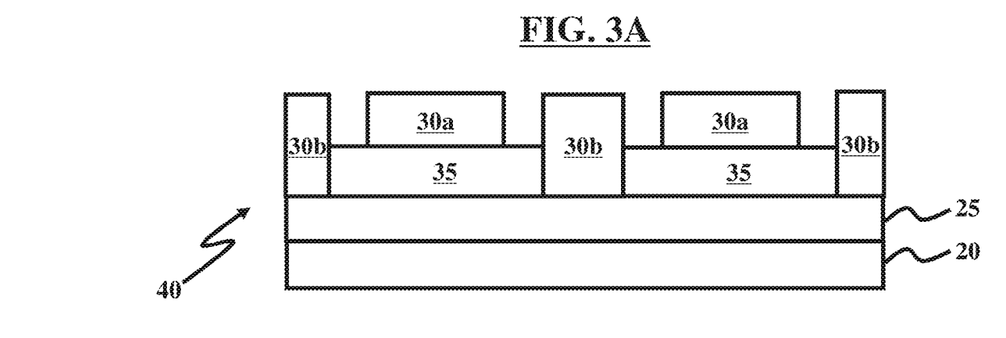
FIG. 3A illustrates a schematic cross-sectional diagram of a combinatorial test sample according to an embodiment herein.
Figure 3B:
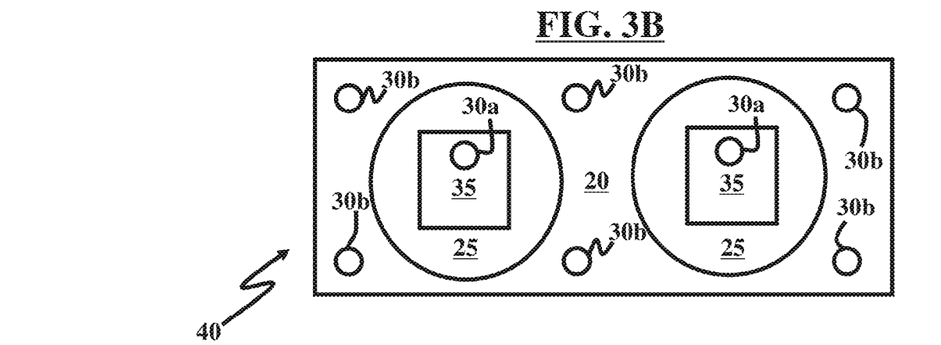
FIG. 3B illustrates a schematic top view diagram of a combinatorial test sample according to an embodiment herein.

FIG. 3A, with reference to FIGS. 1 and 2, illustrates a schematic cross-sectional diagram of a combinatorial test sample (e.g., substrate 40) according to an embodiment herein. Moreover, FIG. 3B, with reference to FIGS. 1 through 3A, illustrates a schematic top view diagram of a combinatorial test sample (e.g., substrate 40) according to an embodiment herein. As discussed above and shown in FIGS. 3A and 3B, substrate 40 includes glass 20, a transparent conducting oxide (TCO) coating 25, electrodes 30a, 30b, and a solar cell 35. In addition, each solar cell 35 of substrate 40 is combinatorially varied. For example, in one embodiment, the combinatorial variation of the solar cells 35 includes varied texturing by wet chemistry or varied thin film deposition by dry process tools. Moreover, for each solar cell 35, electrode 30a includes a metal electrode attached to the area inside solar cell 35 that has the individual separated electrode (e.g., electrode 30a) connecting to the current-voltage source during test. Furthermore, for each solar cell 35, electrode 30b includes a metal area outside of solar cell 35 connected to a common electrode (e.g., electrode 30b) that is further connected to ground.

Figure 4A:
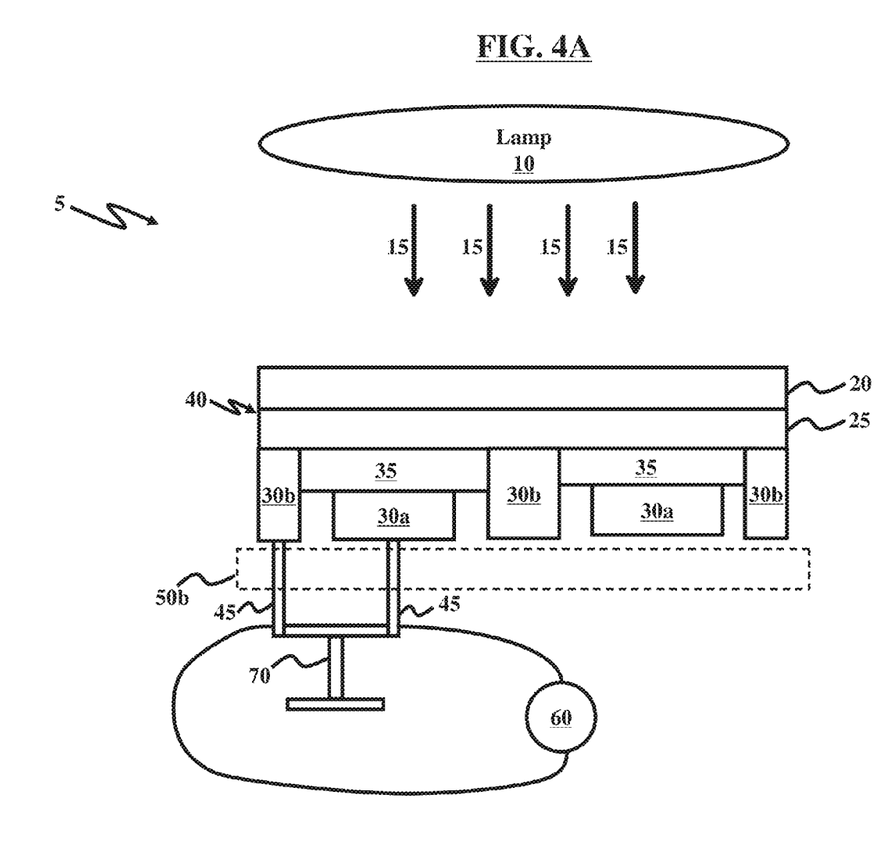
FIG. 4A illustrates a block diagram of a Z-stage combinatorial characterization apparatus according to an embodiment herein.
Figure 4B:
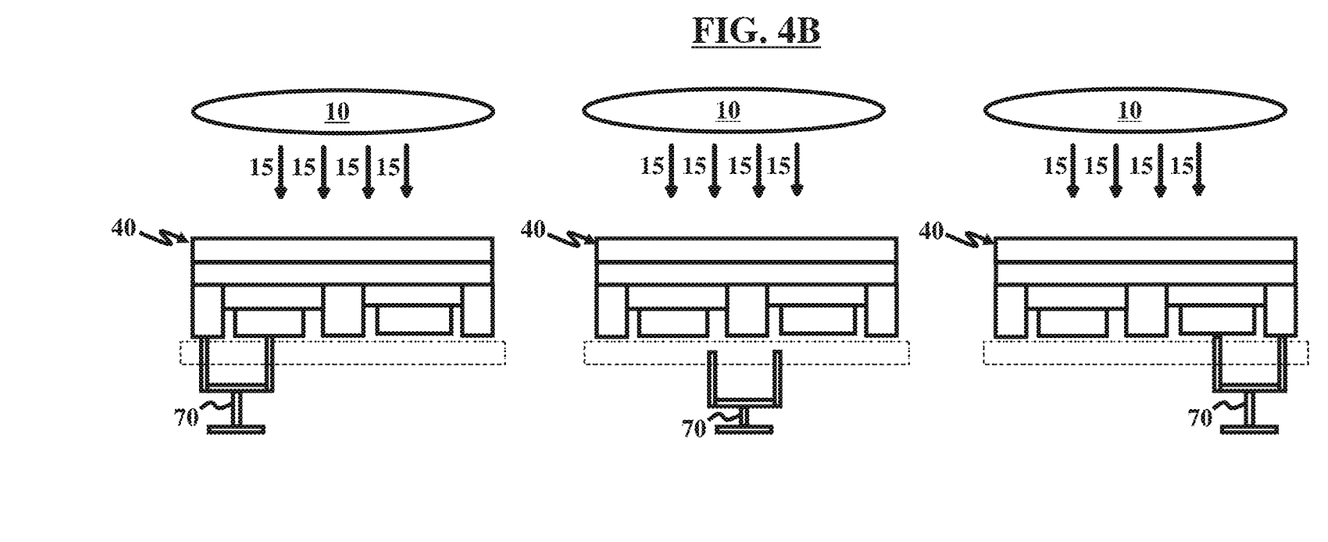
FIG. 4B illustrates a block diagram of a Z-stage combinatorial characterization apparatus in transition according to an embodiment herein.

FIG. 4A, with reference to FIGS. 1 through 3B and 9, illustrates a block diagram of a Z-stage combinatorial characterization apparatus 5 according to an embodiment herein. The embodiments, as described herein, utilize the X, Y, and Z axes to define various geometric planes associated with the components described herein. Those skilled in the art would recognize that the X, Y, and Z axes may be configured in any suitable orientation, and the embodiments herein are not restricted to any particular orientation. As shown in FIG. 4A, Z-stage combinatorial characterization apparatus 5 includes a lamp 10, light 15 (emitted from lamp 10), substrate 40, probes 45, Z-stage device 70 and source meter 60. Z-stage combinatorial characterization apparatus 5 also includes a multi-axis (e.g., X-Y) stage tray 50b. The X-Y stage tray 50b may be cooled by air around the X-Y stage tray 50b.

As described above, substrate 40, according to one embodiment, includes at least one solar cell 35, where solar cell 35 includes glass 20, a transparent conducting oxide (TCO) coating 25, and electrodes 30a, 30b. Also shown in the embodiment of FIG. 4A, all of the electrodes (e.g., electrodes 30a, 30b) are transferred to a back surface (e.g., TCO 25) of substrate 40 where substrate 40 is not exposed to light (e.g., light 15 emitted from lamp 10) in a configuration suitable for backside probing. Again, those of ordinary skill in the art could reverse the configuration shown in FIG. 2 to enable frontside probing. In the embodiment shown in FIG. 4A, each solar cell 35 of substrate 40 can be processed under varied wet (e.g. texturing) or dry (electrode sputtering, absorb layer deposition) conditions during the combinatorial processing (e.g., primary screening process (110), shown in FIG. 1). In the embodiment shown in FIG. 4A and further illustrated above in FIG. 3B, the area inside of solar cell 35 attaches to a positive electrode 30a while the area outside of the solar cell 35 is the common electrical ground (e.g., electrode 30b). According to one embodiment herein, electrodes 30a, 30b are formed by chemical vapor deposition (CVD) and isolated by a light scribing process on substrate 40.

In addition, as shown in FIG. 4A, electrodes 30a, 30b are operatively connected to a selective circuit (e.g., Z-stage device 70). In one embodiment herein, a connection between electrodes 30a and 30b is made through Z-stage device 70, which includes a plurality of probes 45 (e.g., two probes 45 is shown in FIG. 4A) where at least one probe 45 touches the area inside of each solar cell 35 (e.g., electrode 30a) and another probe 45 touches the nearby outside area of each solar cell 35 (e.g., electrode 30b). In addition, as described in further detail below, X-Y stage tray 50b and substrate 40 can be held together by vacuum or by mechanical means, such as a clamp, or a combination of both. With a measurement device (e.g., source meter 60) operatively connected to a selective circuit (e.g., as defined by the contacts made by electrode 30a and 30b on substrate 40), a control program (e.g., as stored and executed by computing device 200 shown in FIG. 9) automatically selects one site (e.g., solar cell 35) on substrate 40 for testing and may continue in series with the next site (i.e., solar cell 35) until all of the sites on substrate 40 are tested.

In FIG. 4A, instead of the geometry-matched switching matrix 50 of multi-pin combinatorial characterization apparatus 1 shown in FIG. 2, only two probes 45 attached to Z-stage device 70 are used with one probe 45 touching the area inside of the solar cell 35 and the other probe 45 contacting the area outside of the solar cell 35. Substrate 40 is also mounted on X-Y stage tray 50b for movement along an X-Y plane (in contrast to the stationary substrate support structure 50a of multi-pin combinatorial characterization apparatus 1 shown in FIG. 2) and probes 45 are fixed onto Z-stage device 70 to provide movement along a Z-plane. After finishing testing a solar cell 35, Z-stage device 70 lowers probes 45 to disconnect probes from electrodes 30a, 30b. Substrate 40 is then moved to the next site (as described below) using X-Y stage tray 50b and the connection to electrodes 30a, 30b is restored (as shown in the sequential diagram in FIG. 4B).

The multi-pin combinatorial characterization apparatus 1 shown in FIG. 2 may be used for parallel testing. The Z-stage combinatorial characterization apparatus 5 shown in FIG. 4A also has good site-to-site repeatability because the light (e.g., lamp 10) is fixed. These embodiments may also be universal for any kind of test substrate and no specific fixture is required, particularly for Z-stage combinatorial characterization apparatus 5 shown in FIG. 4A. Besides the automation, multi-pin combinatorial characterization apparatus 1 can also significantly increase throughput by enabling parallel testing. According to embodiments herein, I-V testing can be automated and the site-isolated regions of a test substrate may be tested in parallel. Consequently, the embodiments herein increase throughput on characterization significantly over the conventional techniques where an operator is manually required to measure each sample. In addition, in one embodiment of multi-pin combinatorial characterization apparatus 1, a multi-channel source meter 60 is coupled to switching matrix 50, where an individual measurement channel is assigned for each solar cell 35 on substrate 40 in order to achieve further throughput gains through parallelism.

In addition, a characterization tool based on multi-pin combinatorial characterization apparatus 1 or Z-stage combinatorial characterization apparatus 5 can optionally measure the temperature of the solar cell 35 currently being measured and correct for any temperature increase that occurs (e.g., due to expose of light 15 from lamp 10) of substrate 40. Alternatively, substrate 40 may be cooled during the characterization of the solar cell 35 to maintain a steady temperature during each measurement. For example, in one embodiment, a heat sink (not shown) is used to cool substrate 40. In yet another alternate embodiment, substrate 40 can be pre-heated to a temperature sufficient to mitigate any ancillary heating, caused by the lamp 10 used during the I-V measurement.

Figure 5A:
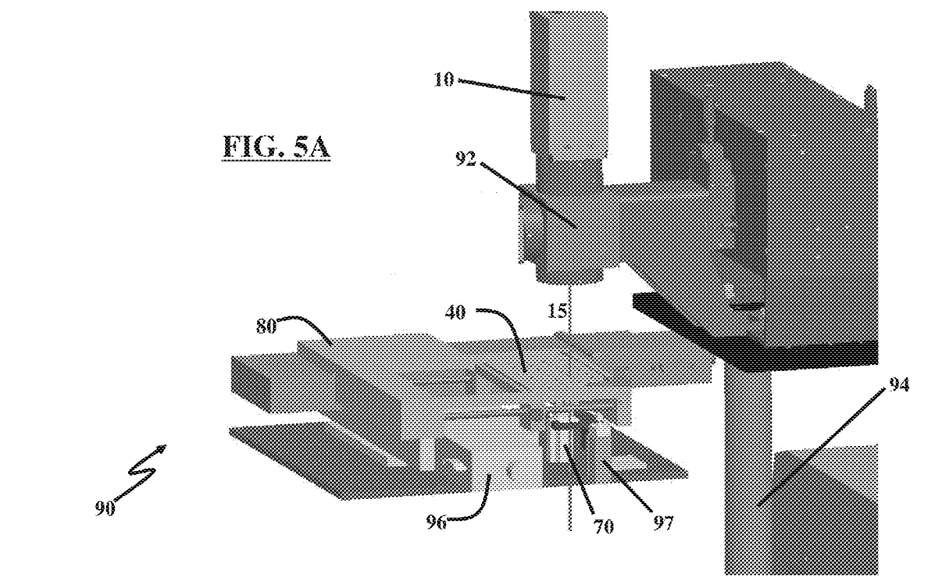
FIG. 5A illustrates a schematic diagram of a current-voltage measurement tool according to an embodiment herein.

FIG. 5A, with reference to FIGS. 1 through 4B, illustrates a schematic diagram of an I-V measurement tool 90 according to an embodiment herein. As shown in FIG. 2, I-V measurement tool 90 includes a full spectrum lamp 10, shutter 92, substrate 40, sample tray 80, support platform 94, and articulation platform 96. Also shown in FIG. 5A is light 15 emitted from full spectrum lamp 10. In the embodiment shown in FIG. 5A, sample tray 80 is located at a fixed distance (e.g., approximately 2-5 inches) from shutter 92. As described in further detail below, one embodiment of articulation platform 96 includes an X-Y stage tray 50b to move sample tray 80 along two axes to enable full coverage of substrate 40 while maintaining a fixed distance from shutter 92. In the embodiment shown in FIG. 5A, I-V measurement tool 90 further includes Z-stage device 70 on articulation platform 96 and under sample tray 80 to move probes 45 (shown in FIG. 4A) along a vertical plane.

Figure 5B:
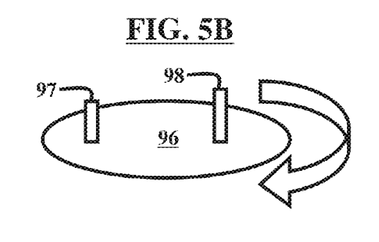
FIG. 5B illustrates a schematic diagram of the rotation of an articulation platform of a current-voltage measurement tool according to an embodiment herein.

I-V measurement tool 90 may further include a transmittance detector 97 (along with Z-stage device 70) on articulation platform 96 and under sample tray 80 to measure the transmittance of a thin film glass solar cell 35 on substrate 40 or the I-V efficiency of an electrochromic material in another potential use of this tool where multiple electrochromic materials are deposited and varied from one another on substrate 40. In such an embodiment, articulation platform 96 rotates (e.g., as shown in FIG. 5B) to align the transmittance detector 97 under solar cell 35 on substrate 40 and shutter 92. Transmittance is useful, for example, when developing electrochromic materials and therefore there is a need to shine light 15 through the substrate 40 to measure the transmittance of the electrochromic material.

Figure 6A:
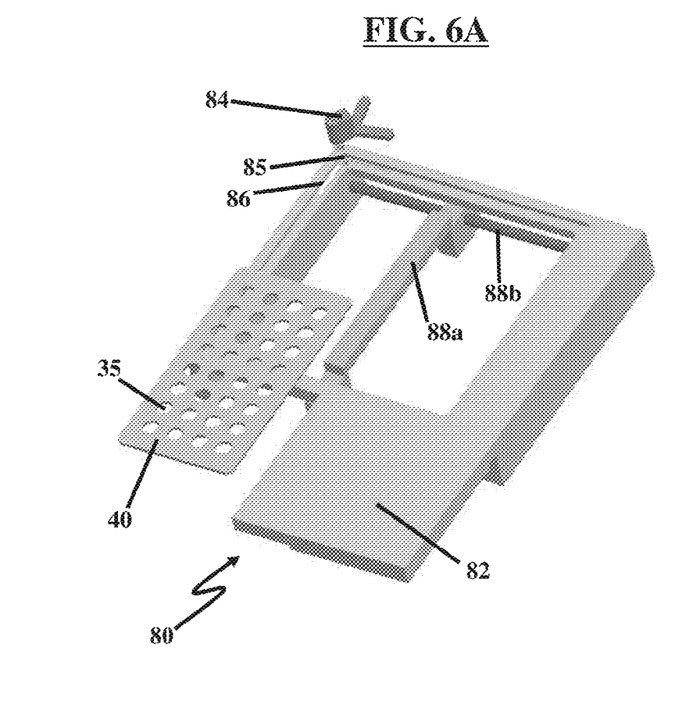
FIG. 6A illustrates a schematic diagram of an unloaded sample tray according to an embodiment herein.
Figure 6B:
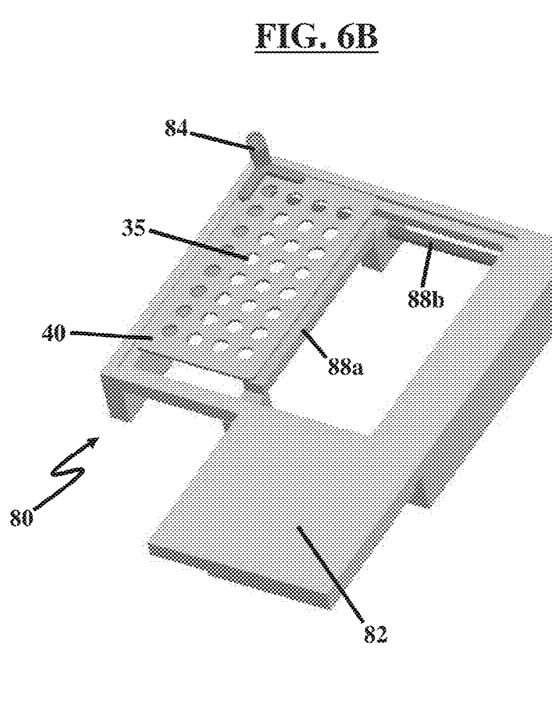
FIG. 6B illustrates a schematic diagram of a loaded sample tray according to an embodiment herein.

FIG. 6A, with reference to FIGS. 1 through 5B, illustrates a schematic diagram of an unloaded sample tray 80 according to an embodiment herein. In addition, FIG. 6B, with reference to FIGS. 1 through 6A, illustrates a schematic diagram of a loaded sample tray 80 according to an embodiment herein. As shown in the embodiment of FIGS. 6A and 6B, sample tray 80 includes a support frame 82 to hold substrate 40, where substrate 40 may include one solar cell 35 or multiple solar cells 35. According to one embodiment herein, when there are multiple solar cells 35 on substrate 40, each solar cell 35 is combinatorially varied. Substrate 40 is held in place by clamp 84, where clamp 84 is secured via channels 86. The channels 86 may be configured as a lip/ledge on which the substrate 40 rests, or the channels 86 may include vacuum-like properties to further retain the substrate 40 thereon. Operatively connected to support frame 82 are sample guides 88a, 88b, which are perpendicularly coupled to each other. In addition, while not shown in FIGS. 6A and 6B, in one embodiment, the sample tray 80 may be temperature controlled to regulate the temperature of the substrate 40 being tested. Substrate 40 is secured to the support frame 82 by positioning the substrate 40 at a corner 85 of the channels 86. The sample guide 88a moves axially and translationally with respect to sample guide 88b and the support frame 82 to accommodate different sizes of substrate 40. Once positioned on the sample guide 88a and aligned in the channel 86, the substrate 40 is locked in place with the clamp 84, which, in one embodiment, may use a vacuum (not shown) to further retain the substrate 40 in place.

Figure 7:
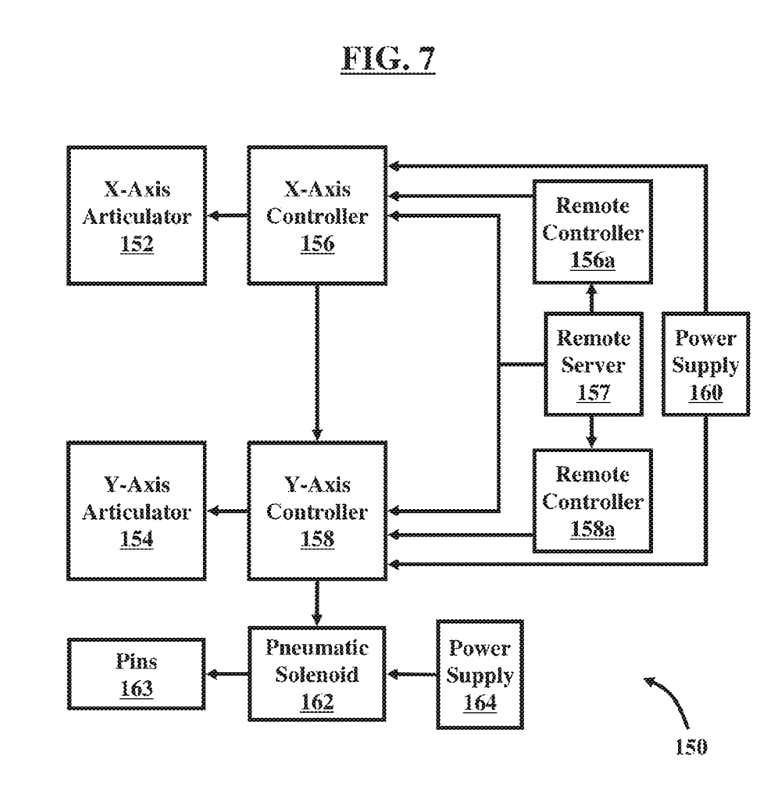
FIG. 7 illustrates a block diagram of a multi-axis control device according to an embodiment herein.

FIG. 7, with reference to FIGS. 1 through 6B and 9, illustrates a block diagram of a multi-axis (e.g., X-Y) control device according to an embodiment herein. As shown in FIG. 7, multi-axis control device 150 includes an X-axis articulator 152 (e.g., a step motor), a Y-axis articulator 154 (e.g., a step motor), an X-axis controller 156 (e.g., SMC100CC controller, manufactured by Newport Corporation, Irvine, Calif., USA), an optional remote controller 156a, a Y-axis controller 158 (e.g., SMC100CC controller, manufactured by Newport Corporation, Irvine, Calif., USA), an optional remote controller 158a, a power supply 160, a pneumatic solenoid 162, and a DC power supply 164. According to one embodiment herein, remote controllers 156a and 158a are operatively coupled to remote server 157 (e.g., computing device 200 shown in FIG. 9) to allow remote control and automation of X-axis controller 156 and Y-axis controller 158, respectively. In addition, according to one embodiment herein, pneumatic solenoid 162 is coupled to a plurality of connectors (e.g., pins 163 or probes 45), which articulate (via pneumatic solenoid 162) to form connections to substrate 40 on articulation platform 96. The pins 163, as shown in FIG. 7, may be configured as push-pins that include a spring at the tip to press against the electrodes of the substrate 40, or they may be sharp tipped stiff pins, or any other type of suitable probe. As shown in FIG. 7, pneumatic solenoid 162 as well as X-axis controller 156 and Y-axis controller 158 are coupled to power supplies (i.e., power supply 160 and power supply 164, respectively). While shown in FIG. 7 as two separate power supplies, (e.g., power supply 160 and power supply 164), the embodiments herein are not limited to such a configuration and those of ordinary skill in the art could easily consolidate power supply 160 and power supply 164 into a single power supply connected to pneumatic solenoid 162 as well as X-axis controller 156 and Y-axis controller 158.

Moreover, according to one embodiment herein, multi-axis control device 150 is operatively coupled to articulation platform 96 (shown in FIG. 5A, which may include X-Y stage tray 50b shown in FIG. 4A) and sample tray 80 to move sample tray 80 (shown in FIGS. 5 through 6B) along an X-axis and/or along a Y-axis. In so doing, multi-axis control device 150 moves substrate 40 (shown in FIG. 2) along a plane that is located at a fixed distance from shutter 92 (shown in FIG. 5A) to vertically align specially treated portions (e.g., solar cell 35) of substrate 40 with shutter 92. In another embodiment, the articulation platform 96 is actively cooled by air around the articulation platform 96.

The specially treated portions of substrate 40 may include portions (e.g., solar cell 35) prepared using combinatorial processing. For example, combinatorial processing provides rapid evaluation of solar processing operations. Some exemplary solar processing operations include operations for adding (depositions) and removing layers (etching), defining features, preparing layers (e.g., cleans), doping, etc. In such an embodiment, the systems supporting the combinatorial processing are flexible to accommodate the demands for running the different processes either in parallel, serial, or some combination of the two. It is to be understood that the embodiments herein are not limited to the combinatorial development and testing of solar cells 35, but may also be used to test electrochromic materials, photochromic materials, thermochromic materials, etc.

As used herein, combinatorial processing may include any processing (e.g., solar processing) that varies the processing conditions in two or more regions of a substrate 40. A substrate 40 may be, for example, a silicon substrate 40 such as a wafer that is used in solar processing. A region of a substrate 40 may be any portion of the substrate 40 that is somehow defined, for example by dividing the substrate 40 into regions having predetermined dimensions or by using physical barriers, such as sleeves, over the substrate 40. The region may or may not be isolated from other regions. For example, a substrate 40 may be divided into two or more regions, each of which may or may not include solar cell structures 35 (e.g., Cu$_2$ZnSnS$_4$ solar cell structures and copper indium gallium diselenide solar cell structures may occupy separate regions).

A process may be performed at each of the regions. For example, a first region is cleaned using a first cleaning agent, and a second region is cleaned using a second cleaning agent. The efficacies of the two cleaning agents are evaluated, and none, one, or both of the cleaning agents may be selected as suitable candidates for larger scale processing (e.g., on regions with structures, or regions enabling more sophisticated testing, or a full substrate, etc.). According to other examples, multiple iterations of the same experiment are performed on the same substrate 40, and any number of regions may be defined. For example, five cleaning solutions may be tested using fifteen regions of a substrate 40, each cleaning solution being tested three times.

Figure 8:
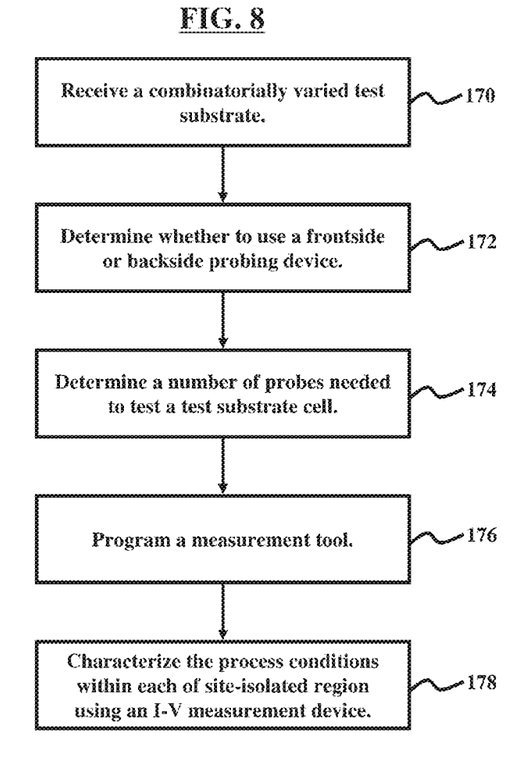
FIG. 8 illustrates a flowchart of a method according to an embodiment herein.

FIG. 8, with reference to FIGS. 1 through 7 and 9, illustrates a flow diagram according to an embodiment herein. Step (170) of the method of FIG. 8 includes receiving a combinatorially varied test substrate (e.g., substrate 40 shown in FIG. 1). Step (172) includes determining whether to use a frontside or backside probing device (e.g., thin film solar cells and LED's would use backside probing device, such as Z-stage combinatorial characterization apparatus 5 shown in FIG. 4A and CIGS or CZTS solar cells would use frontside probing device (not shown)). Step (174) includes determining a number of probes (e.g., probes 45) needed to test a test substrate cell (e.g., solar cell 35 shown in FIG. 3B). Furthermore, step (176) includes programming a measurement tool (e.g., Z-stage combinatorial characterization apparatus 5 shown in FIG. 4A), which includes the locations (e.g., coordinates of the multiple process conditions within the site-isolated regions (e.g., solar cell 35) of the test substrate (e.g., substrate 40) and the thickness of each process condition at the site-isolated regions (e.g., solar cell 35) to achieve good contact between the probes 45 and the electrodes (e.g., electrodes 30a, 30b). Step (178) of the method shown in FIG. 8 characterizes the process conditions within each of site-isolated region (e.g., solar cell 35) using an I-V measurement device (e.g., Z-stage combinatorial characterization apparatus 5 shown in FIG. 4A).

A representative hardware environment for practicing the embodiments herein is depicted in FIG. 9, with reference to FIGS. 1 through 8. This schematic drawing illustrates a hardware configuration of an information handling/computer system 200 (e.g., for programming a measurement tool as described in step (176) of FIG. 8) in accordance with the embodiments herein. The system 200 comprises at least one processor or central processing unit (CPU) 210. The CPUs 210 are interconnected via system bus 212 to various devices such as a random access memory (RAM) 214, read-only memory (ROM) 216, and an input/output (I/O) adapter 218. The I/O adapter 218 can connect to peripheral devices, such as disk units 211 and tape drives 213, or other program storage devices that are readable by the system 200. The system 200 can read the inventive instructions on the program storage devices and follow these instructions to execute the methodology of the embodiments herein. The system 200 further includes a user interface adapter 219 that connects a keyboard 215, mouse 217, speaker 224, microphone 222, and/or other user interface devices such as a touch screen device (not shown) to the bus 212 to gather user input. Additionally, a communication adapter 220 connects the bus 212 to a data processing network 225, and a display adapter 221 connects the bus 212 to a display device 223 which may be embodied as an output device such as a monitor, printer, or transmitter, for example.

Embodiments herein provide a measurement tool (e.g., I-V measurement tool 90) that permits a sample (e.g., as prepared using combinatorial processes on substrate 40) to be loaded once and all other testing functions association with current-voltage measurements to be automated. In addition, such automation provides greater efficiency (e.g., less time to conduct the measurements because both the current-voltage measurements are performed without human intervention) over conventional systems. Embodiments herein also provide greater throughput (e.g., performing multiple measurements in parallel) and greater accuracy (e.g., programmable control of a sample).

The embodiments herein provide a measurement tool (e.g., I-V measurement tool 90) that permits a sample (e.g., as prepared using combinatorial processes) to be loaded once and all other testing functions in association with current-voltage measurement to be automated. In addition, such automation provides greater efficiency (e.g., less time to conduct the measurements) over conventional systems, which would be advantageous for any research and development but may be of particular value in improving the throughput for combinatorial testing. The speed at which the solar cells 35 are characterized is valuable in achieving high performance combinatorial processing. Embodiments herein also provide greater precision and greater accuracy of the measurements.

One embodiment of the combinatorial screening process described above (e.g., FIG. 1) enables multiple experiments to be performed on a single substrate 40 and the rapid evaluation of solar cell processing operations and solar cell materials. Multiple solar cells 35 may reside on a single substrate 40 and are designed to run the different combinatorial processes either in parallel, serial, or some combination of the two. For example, embodiments herein allow forming different types of thin film solar cells, CZTS solar cells, CIGS solar cells, and cadmium telluride (CdTe) solar cells that can be combinatorially varied and evaluated. These methodologies all incorporate the formation of site-isolated regions using a combinatorial processing tool and the use of these site-isolated regions to form the solar cell area. Therefore, multiple solar cells 35 may be rapidly formed on a single substrate 40 for use in combinatorial methodologies. Any of the individual processes of the methods described herein may be varied combinatorially to test varied process conditions or materials.

The use of combinatorial-based rapid device prototyping methods (e.g., as shown in FIG. 1) permits fabrication, comprehensive characterization, and analysis of hundreds of unique solar cells 35 on a weekly basis to dramatically increase learning rates. Alternative device structures, process integration schemes, and material compositions are systematically explored at speeds that would otherwise be impossible using traditional methods and tools. This pace of development applied to Earth-abundant TFPV devices may represent an order of magnitude acceleration of R&D in this area.

For example, CZTS is a compound semiconductor that evolves from the chalcopyrite structured I-III-VI2 compound CIGS, where indium/gallium is substituted by zinc/tin and selenium by sulfur. The substituted elements in CZTS are comparatively orders of magnitude more abundant than CIGS elements. CZTS has a band gap between approximately 1.45 and 1.6 eV, which is very close to the optimum value of an absorber layer of a solar cell 35. Additionally, the band edge absorption coefficient of CZTS is above $1 \times 10^4$ cm$^{-1}$ which enables its use as a thin film solar cell absorber candidate.

A standard CZTS device structure may include the deposition of four primary layers on a substrate: a back contact (e.g., Mo), an absorber layer (e.g., CZTS), a buffer layer (e.g., CdS or ZnS), and a front contact (e.g., ITO or Al:ZnO). Each material and deposition process provides an opportunity to reduce manufacturing costs and increase cell efficiencies by using the combinatorial process described herein. Moreover, the similarity in process flow relative to current CIGS processes offers the intriguing possibility of retrofitting legacy production assets to produce lower cost devices using more environmentally friendly, Earth-abundant materials.

Various techniques can be used for depositing the CZTS absorber layer, which is the most critical layer in the device stack. These techniques include electron beam deposition continued by sulfurization, hybrid sputtering, vacuum evaporation with sulfurization, sol-gel followed by $H_2Se$ annealing, pulsed laser deposition, sputtering followed by sulfurization, single step RF sputtering, electroplating, and spray pyrolysis.

As described above, the embodiments herein improve the combinatorial screening and the characterization of compounds (e.g., CIGS absorption layers, CZTS absorption layers, and other chalcopyrite structured I-III-VI2 compound CIGS absorption layers) after the application of those formulations. For example, during an initial screening (e.g., primary screening process ((110)) shown in FIG. 1), many samples (e.g., 18 spots or 46 spots on a single wafer, where each spot is a unique material composition) are created using blanket films (e.g., as supplied by Advantiv Technologies, Inc. Fremont Calif., USA) and thereafter tested. This initial screening (e.g., primary screening process (110)) may have a simple criteria (e.g., maximizing current versus voltage measurements for a narrow wavelength band) to allow a quick evaluation and thereby quickly rule out materials that will not undergo the second stage of testing (e.g., in secondary screening process ((120)) shown in FIG. 1). During the secondary screening process ((120)) shown in FIG. 1, a variety of more specific characterization methods may be performed on the test cleaning formulations identified in primary screening process ((110)) on fabricated patterned/metallized surfaces. Such characterization methods include parametric tests and reliability tests. Sample criteria to evaluate include, but are not limited to: maximizing current density, maximizing current versus voltage measurements, for a narrow wavelength band, and maximizing current versus voltage measurements for the bandwidth of sunlight.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of several embodiments, those skilled in the art will recognize that the embodiments herein can be practiced with modification within the spirit and scope of the appended claims.

What is claimed is:

1. An apparatus for measuring current-voltage (I-V) characteristics, said apparatus comprising:
    a lamp configured to emit light;
    a substrate support structure configured to support a substrate, the substrate comprising a plurality of solar cells,
    a plurality of positive electrodes, each of the plurality of positive electrodes being operatively connected to one of the plurality of solar cells, and at least one negative electrode peripherally deposited around each of the plurality of solar cells;
    a multi-probe switching matrix comprising a plurality of probes, wherein each probe is individually articulable;
    a programmable switch box operatively coupled to the multi-probe switching matrix and configured to selectively articulate each of the plurality of probes such that the probes are moved to contact at least one of the plurality of positive electrodes and the at least one negative electrode and re-moved until contact is lost with the at least one of the plurality of positive electrodes and the at least one negative electrode; and
    a source meter operatively coupled to the programmable switch box and configured to measure the I-V characteristics of the substrate.

2. The apparatus of claim 1, wherein the lamp comprises a solar simulator and the light comprises natural light with less than 1% difference of sunlight.

3. The apparatus of claim 1, further comprising a computing device operatively coupled to the programmable switch box, wherein the computing device instructs the programmable switch box to articulate a single positive electrode specific to a first of the plurality of solar cells and a single negative electrode specific to the first of the plurality of solar cells.

4. The apparatus of claim 1, wherein the source meter comprises a multi-channel source meter and each channel of the multi-channel source meter is coupled to the programmable switch box.

5. The apparatus of claim 1, wherein each probe comprises a spring-loaded pin.

6. The apparatus of claim 1, further comprising a pneumatic solenoid coupled to the multi-probe switch matrix, wherein the pneumatic solenoid articulates each probe using a pneumatic pressure.

7. The apparatus of claim 1, wherein each of the plurality of solar cells is formed using combinatorially varied process conditions, the process conditions comprising at least one of texturing by wet chemistry and varied thin film deposition by dry processing.

8. A current-voltage (I-V) characterization tool comprising:
    a lamp configured to emit light;
    an X-Y stage tray configured to support a substrate, the substrate comprising a plurality of site-isolated regions;
    a shutter positioned between the lamp and the X-Y stage tray, wherein the shutter is configurable into an open position allowing the light to pass therethrough to the substrate and a closed position blocking the light from passing to the substrate;
    a multi-axis control device operatively coupled to the X-Y stage tray, wherein the multi-axis control device is configured to articulate the X-Y stage tray along a plane parallel to the X-Y stage tray;
    a Z-stage device comprising at least two probes, wherein the Z-stage device is configured to articulate in a direction perpendicular to the X-Y stage tray;
    a source meter operatively coupled to the Z-stage device, wherein the source meter is configured to measure a current from the substrate; and
    a computing device operatively coupled to the Z-stage device, the shutter, and the X-Y stage tray, wherein said computing device is configured to transmit first movement instructions to the Z-stage device and the X-Y stage tray thereby positioning one of the plurality of site-isolated regions of the substrate below the shutter when the shutter is configured in the closed position and further configured to transmit second movement instructions to the shutter to reconfigure the shutter into the opening position when the one of the plurality of site-isolated regions is positioned below the shutter.

9. The I-V characterization tool of claim 8, wherein each of the plurality of solar cells is formed using combinatorially varied process conditions, the process conditions comprising at least one of texturing by wet chemistry and varied thin film deposition by dry processing.

10. The I-V characterization tool of claim 8, further comprising a pneumatic solenoid coupled to the Z-stage device and the computing device, wherein the pneumatic solenoid articulates the Z-stage device using pneumatic pressure upon receiving the first movement instructions from the computing device.

11. The I-V characterization tool of claim 9, wherein the substrate comprises a plurality of solar cells, a plurality of positive electrodes, each of the plurality of positive electrodes being operatively connected to one of the plurality of solar cells, and at least one negative electrode peripherally deposited around each of the plurality of solar cells, wherein the probes are spaced apart such that each probe contacts at least one of the plurality of positive electrodes and the at least one negative electrode when the Z-stage device is articulated.

12. The I-V characterization tool of claim 8, further comprising a clamp configured to secure the substrate to the X-Y stage tray.

13. The I-V characterization tool of claim 8, further comprising vacuum means for securing the substrate to the X-Y stage tray.

14. The I-V characterization tool of claim 8, wherein the X-Y stage tray comprises:
    an X-axis articulator;
    an X-axis controller coupled to the X-axis articulator;
    a Y-axis articulator; and
    a Y-axis controller operatively coupled to the X-axis controller and the Y-axis articulator.

15. The I-V characterization tool of claim 14, further comprising:
    a first remote controller operatively coupled to the X-axis controller and the computing device, wherein the first remote controller controls the X-axis controller in accordance with the first movement instructions received from the computing device; and
    a second remote controller operatively coupled to the Y-axis controller and the computing device, wherein the second remote controller controls the Y-axis controller in accordance with the first movement instructions received from the computing device.

16. A method of measuring current-voltage (I-V) characteristics of a substrate, the method comprising:
    receiving a substrate, the substrate comprising a plurality of solar cells, a plurality of positive electrodes, each of the plurality of positive electrodes being operatively connected to one of the plurality of solar cells, and at least one negative electrode peripherally deposited around each of the plurality of solar cells;
    emitting light onto the substrate;
    positioning a multi-probe switching matrix relative to the substrate, the multi-probe switching matrix comprising a plurality of probes, wherein each probe is individually articulable;
    selectively articulating each of the plurality of probes such that the probes are moved to contact at least one of the plurality of positive electrodes and the at least one negative electrode and re-moved until contact is lost with the at least one of the plurality of positive electrodes and the at least one negative electrode; and
    measuring the I-V characteristics of the substrate with a source meter.

17. The method of claim 16, wherein the light comprises natural light with less than 1% difference of sunlight.

18. The method of claim 16, wherein the selectively articulating each of the plurality of probes is performed with a programmable switch box, the programmable switch box being operatively coupled to the multi-probe switching matrix.

19. The method of claim 18, wherein the source meter comprises a multi-channel source meter and each channel of the multi-channel source meter is coupled to the programmable switch box.

20. The method of claim 16, wherein each of the plurality of solar cells is formed using combinatorially varied process conditions, the process conditions comprising at least one of texturing by wet chemistry and varied thin film deposition by dry processing.

* * * * *